United States Patent
Eberle et al.

(10) Patent No.: US 9,562,214 B2
(45) Date of Patent: Feb. 7, 2017

(54) CONDITIONING CHAMBER FOR STORING SAMPLES IN A TIME-CONTROLLED MANNER AND METHOD FOR STORING SAMPLES IN A TIME-CONTROLLED MANNER

(75) Inventors: Klaus-Guenter Eberle, Tuttlingen (DE); Gavin Clarke, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 0 days.

(21) Appl. No.: 13/885,149

(22) PCT Filed: Nov. 17, 2011

(86) PCT No.: PCT/EP2011/070399
§ 371 (c)(1),
(2), (4) Date: Jul. 5, 2013

(87) PCT Pub. No.: WO2012/066101
PCT Pub. Date: May 24, 2012

(65) Prior Publication Data
US 2014/0030802 A1   Jan. 30, 2014

(30) Foreign Application Priority Data
Nov. 17, 2010  (DE) .................. 10 2010 060 634

(51) Int. Cl.
C12M 1/00     (2006.01)
C12M 3/00     (2006.01)
(Continued)

(52) U.S. Cl.
CPC .............. *C12M 33/00* (2013.01); *B01L 1/025* (2013.01); *C12M 23/10* (2013.01); *C12M 23/48* (2013.01);
(Continued)

(58) Field of Classification Search
CPC ........... B01L 1/025; B01L 7/00; C12M 33/00; G01N 2035/00356; G01N 2035/00445; G01N 2035/0093; G01N 2035/0427; G01N 2035/0441; G01N 2035/0455; G01N 2035/0465; G01N 35/00; G01N 35/0099; G01N 35/025
(Continued)

(56) References Cited

U.S. PATENT DOCUMENTS 6,475,776 B1 * 11/2002 Higuchi ..................... 435/303.3
2003/0031602 A1   2/2003 Weselak et al.
(Continued)

FOREIGN PATENT DOCUMENTS

DE          10009555 A1   3/2001
DE          10119650 A1   10/2002
(Continued)

OTHER PUBLICATIONS

European Patent Office, International Search Report, May 24, 2012, International Application No. PCT/EP2011/070399, International Filing Date: Nov. 17, 2011, Priority Date: Nov. 17, 2010, Applicant: Andreas Hettich GmbH & Co. KG, pp. 1-4.
(Continued)

*Primary Examiner* — Nathan Bowers
*Assistant Examiner* — Lydia Edwards
(74) *Attorney, Agent, or Firm* — Woodling, Krost and Rust

(57) ABSTRACT

The invention relates to an air-conditioning space (10) for storing samples in a time-controlled manner, comprising a device (22) for automatically feeding sample containers (18) into a climatically sealed space (12) having at least one wall (43), into which a sample container (18) can be inserted into the climatically sealed space (12) through an opening (40, 42), wherein the feed device (22) has at least one drive and
(Continued)

Figure 1:
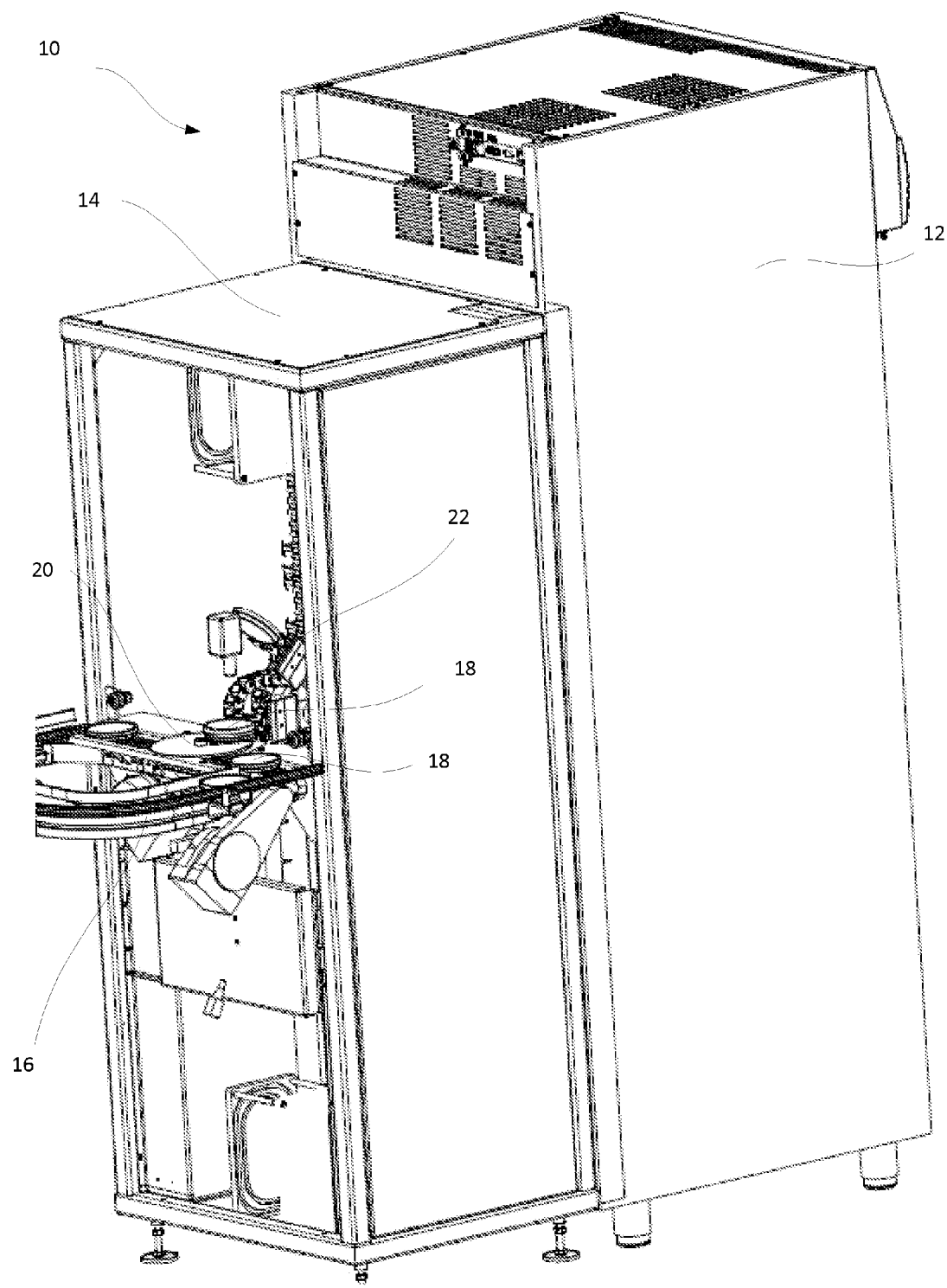

control unit, and an incubator receptacle (30) for receiving the samples (18) is provided inside the climatically sealed space (12). The invention is distinguished by the fact that the feed device has an automatic feed arm (22, 24) which grips a sample container (18) from a receiving position outside the climatically sealed space (12) and deposits the sample container (18) there in a clear deposit position in an incubator receptacle (30).

18 Claims, 3 Drawing Sheets

(51) Int. Cl.
    *C12M 1/14*     (2006.01)
    *C12M 3/04*     (2006.01)
    *C12M 1/26*     (2006.01)
    *B01L 1/02*     (2006.01)
    *G01N 35/00*     (2006.01)
    *C12M 1/22*     (2006.01)
    *B01L 7/00*     (2006.01)
    *G01N 35/02*     (2006.01)
    *G01N 35/04*     (2006.01)

(52) U.S. Cl.
    CPC ............ *C12M 23/50* (2013.01); *C12M 41/14* (2013.01); *C12M 45/22* (2013.01); *G01N 35/00* (2013.01); *B01L 7/00* (2013.01); *G01N 35/0099* (2013.01); *G01N 35/025* (2013.01); *G01N 2035/0093* (2013.01); *G01N 2035/00356* (2013.01); *G01N 2035/00445* (2013.01); *G01N 2035/0427* (2013.01); *G01N 2035/0441* (2013.01); *G01N 2035/0455* (2013.01); *G01N 2035/0465* (2013.01)

(58) Field of Classification Search
    USPC .......................................... 435/283.1–309.4
    See application file for complete search history.

(56) References Cited

U.S. PATENT DOCUMENTS

2004/0256963 A1\*   12/2004   Affleck et al. ................ 312/209
2006/0257999 A1\*   11/2006   Chang et al. .............. 435/289.1

FOREIGN PATENT DOCUMENTS

| DE | 10304012 B4 | 5/2007 |
|---|---|---|
| EP | 0293782 A1 | 5/1988 |
| EP | 1757882 A2 | 2/2007 |
| WO | 9119199 A1 | 12/1991 |
| WO | 02059251 A2 | 8/2002 |
| WO | 2007095366 A2 | 8/2007 |
| WO | 2010001873 A1 | 1/2010 |

OTHER PUBLICATIONS

European Patent Office, Translation of the International Search Report, May 24, 2012, International Application No. PCT/EP2011/070399, International Filing Date: Nov. 17, 2011, Priority Date: Nov. 17, 2010, Applicant: Andreas Hettich GmbH & Co. KG, pp. 1-3.

European Patent Office, PCT Written Opinion, May 24, 2012, International Application No. PCT/EP2011/070399, International Filing Date: Nov. 17, 2011, Priority Date: Nov. 17, 2010, Applicant: Andreas Hettich GmbH & Co. KG, pp. 1-6.

European Patent Office, Office Action, Jun. 22, 2015, pp. 1-5, Application No. 11793695.5-1553, Applicant: Andreas Hettich GmbH & Co. KG.

\* cited by examiner

CONDITIONING CHAMBER FOR STORING SAMPLES IN A TIME-CONTROLLED MANNER AND METHOD FOR STORING SAMPLES IN A TIME-CONTROLLED MANNER

This patent application is the national phase entry of PCT/EP2011/070399. PCT/EP2011/070399, international application filing date Nov. 17, 2011, claims the benefit and priority of and to German patent application no. DE 10 2010 060 634.0, filed Nov. 17, 2010. PCT/EP2011/070399, international application filing date Nov. 17, 2011, and German patent application no. DE 10 2010 060 634.0, filed Nov. 17, 2010, are incorporated herein by reference hereto.

The invention relates to a conditioning chamber and a method for storing samples in a time-controlled manner.

Known from the prior art are automatic feed devices for incubators which introduce large numbers of samples contained in sample dishes into an incubation chamber in order to achieve an as high as possible storage density. For time-controlled storage, reloading systems are integrally provided inside the incubation chamber, for example conveyor belt systems.

The shortcoming of these solutions is that—although they achieve a high packing density—the conveyor systems integrated in the incubator are difficult to clean in case of contamination, on the one hand, and they do not allow for single samples to be removed individually, on the other. Samples can only be removed as the conveyor system proceeds and only in the order determined by the conveyor system.

Disclosed in EP 0 293 782 A1 is an incubator which comprises a storage system designed as a carousel conveyor.

Disclosed in DE 103 04 012 B4 is a climatic chamber having object storage means and an internal transport device. According to this printed document, an object to be stored is transferred from an external transport device to an internal transport device and an internal transport device then stores the object at its predetermined storage position.

WO 02/059 251 A2 also discloses a climatic storage chamber which includes a carousel that is stationary in a vertical direction but rotatable, and can be loaded automatically by means of a feed device. In this embodiment, the feed/loading device is located within the climatic chamber.

DE 100 09 555 A1 likewise discloses a climatic chamber which can be loaded automatically. Said chamber also has a storage system that is vertically rigid. Furthermore, the climatic chamber includes a transport means which is located within the climatic chamber. This transport means stores the samples in their respective compartments after they have been introduced into the climatic chamber.

The above mentioned embodiments are advantageous in that the transport means provided within the incubator can easily reach the various storage positions which differ above all in their vertical locations.

However, their disadvantage is that they require transport means to be provided within the climatic chamber which will adversely affect the conditions prevailing within the climatic chambers, due to its drives. On the one hand, this may be caused by the wear and tear of mechanical components, or by the generation of heat by the motors, on the other.

It is the object of the present invention to provide a device which allows a high packing density to be obtained, which can be cleaned easily and which allows individual samples to be removed in a time-controlled manner.

In a known manner, a conditioning chamber for time-controlled storage comprises a device for automatically feeding and withdrawing sample containers in a climatically sealed chamber having at least one wall. The sample containers can be introduced into the climatically sealed chamber through at least one opening thereof. The automatic feed device has at least one drive and control unit.

Furthermore, an incubator receptacle for receiving the samples is provided inside the conditioning chamber. The vertical extension of the incubator receptacle is stationary and/or limited.

In accordance with the invention, the feed or withdrawal device has a gripper which grips a sample container from a receiving position outside the climatically sealed chamber and places the sample container at a unique storage position. In this case, the feed device is located outside the conditioning chamber. The sample containers can be individually withdrawn by means of the gripper.

The fact that the sample containers are individually fed and placed at a unique storage position by the gripper for example allows the sample containers introduced into the climatic chamber to be incubated for individually specified periods of time, and it is also possible to perform an interim analysis of the current state of each sample.

The fact that the samples are placed inside the chamber using a gripper introduced into the climatic chamber from the outside, the incubator receptacle may be of a very simple design, thus making it easy to clean. Arranging the feed device outside the climatic chamber additionally avoids contamination of the climatic chamber from the very start as well as prevents the introduction of heat or cold into the chamber.

In a first advantageous embodiment the gripper may have a joint which ensures that the sample container gripped in the receiving position can be turned and then placed in the incubator receptacle. The rotary movements to be performed on the sample container may require a lot of space, depending on the geometry of the sample container. By arranging the feed and withdrawal device and the gripper outside the climatic chamber, no climatic chamber space has to be sacrificed to accommodate such rotary movements of the sample container. The alignment of the sample container may thus be performed outside the climatic chamber by the feed and withdrawal device.

As a result, the samples can quickly be placed in storage in their proper orientation. This measure is particularly advantageous for cultures grown in Petri dishes as condensed water formed in the climatisation process will not drip onto the culture medium contained in the Petri dish and thus affect the growth of the cultures but will remain in the lid and/or will be collected until it has volatized. This ensures higher reliability and a better sample quality.

As samples will be rotated automatically, human intervention will no longer be required for the further processing of the samples after the culture has been applied onto the culture medium. This will eliminate human error. On the one hand, this allows optimal in-line treatment in combination with a connectable device for automatic sample application, on the other hand this prevents storage errors.

For improved reliability, a position determining device may be provided which assesses the position of a sample container, in particular a Petri dish, in the receiving position. The sample container will thus only be rotated by the gripper if required as it is being introduced into the climatically sealed chamber. If a sample container is already in a rotated position in the receiving position, it may either be introduced into the climatically sealed chamber without having to be rotated again or can be removed for inspection by qualified personnel. The position determining device may be a simple light barrier, depending on the design of the Petri dishes used.

In a particularly advantageous embodiment of the invention, the gripper connected to a feed arm is mounted on a moving device which is used to move the gripper to different vertical positions. This allows gripped samples to be placed at different levels and thus significantly increases the number of samples that can be placed at a unique position each without resulting in a complex design of the incubator receptacle. In addition, a higher access speed can be reached by adjusting the vertical position of the gripper device and not the incubator receptacles storing the samples. Furthermore, the gripper may be provided on a horizontally movable support or a horizontally movable feed arm to move a sample horizontally into the climatic chamber.

For the generation of time data, a bar code reader may be provided on the receiving device in the receiving area, which reader will allow an individual time to be set for storing the individual sample containers based on the bar code information on each sample. This bar code or other kind of identification label also allows a unique and fully automated storage based on such identification data. Moreover, it can be verified whether the sample has been introduced into the correct climatic chamber and is being treated there.

The interface obtained between the climatic chamber and non-climatic space may essentially be formed such that in the separation between the climatic chamber and non-climatic space there is always an opening through which the feed arm/gripper can pass into the chamber to be conditioned.

This opening may extend over the entire height of the incubator, thus allowing the incubator to be loaded over this entire area. In order to allow ideal conditioning of the climatic chamber, at the same time preventing undesired heat or cold losses and thus a waste of energy, a cover is provided for the vertical opening which may be opened if required.

Preferably this cover is designed such that it will only leave an absolutely necessary opening uncovered, and this opening can be vertically moved to allow the feeding or withdrawal of sample containers. It may be implemented such that a through passage at its upper and lower ends is connected to a roller blind-type cover which is wound around bottom and top rollers. This allows a maximum vertical movement range to be obtained which leaves the through passage only minimally open. This opening will not adversely affect the climatic conditions.

As an additional safeguard, a sensor may be provided which will check whether the storage position assigned by the data processing device is actually free.

A further embodiment of the invention suggests a closure for the through passage which will close the through passage after samples have been removed or introduced.

In yet another advantageous embodiment, the incubator receptacle is in the form of a rotary carousel which allows better use of space with a simplified set-up. When a carousel is used, the gripper will only have to move to a position near the opening and still accomplish a high packing density as the rotation of the carousel will always allow a sample to be placed at a specific position or to be removed therefrom. Advantageously, the position of a sample will be indicated by a data processing device so as to allow unique and fast access. The following parameters may for example be specified for positioning samples in a carousel. One parameter is an angle of rotation of the carousel and the other is a plane—which allows a sample to be uniquely allocated to a specific position.

In a particularly advantageous embodiment, the samples are constituted by a Petri dish.

The through passage may advantageously include an opening through which the Petri dish may be introduced in a horizontal position. Similarly, the incubator receptacle for receiving the Petri dishes is also in a horizontal position. The Petri dishes may only be placed into the individual carousel compartments at the periphery thereof. This has the advantage that the feed device may be of a very simple design and yet ensure unique allocation, at the same time allowing a high packing density to be achieved under given framework conditions.

To ensure automatic analysis and assessment of the samples, a desktop detector, in particular a CCD camera, may be provided near the feed device which will verify the samples before they are introduced into the chamber and will store the results obtained in a data processing system. Furthermore, samples may be removed from the climatic chamber after a predetermined period of time and again be fed to the analysis device so as to allow a comparison of the sample development during the storage time.

This digitized sample analysis is advantageous in that it is stored on a server and can thus be accessed by a plurality of people, in particular on-line, or can also be sent to certain people.

In addition, the subject matter of the invention comprises a method for automatically storing samples in a climatic chamber in a time-controlled manner in which samples are automatically introduced into the climatic chamber and removed again therefrom after a certain period of time.

According to the invention, each sample container will be assigned at least one individual time period after which the sample container or the sample will be removed again after storage. Each sample container will be allocated a free space in a storage system as it is being introduced into the system.

In an advantageous step of the method, the sample containers may be rotated before they are introduced into the climatic chamber.

Samples marked with a bar code will preferably be read out before storage. Depending on the information contained in the bar code, such will be forwarded to a data processing device for further processing. The bar code may contain information on the storage intervals, the relevant contact persons or the allocation to a specific climatic chamber.

What is particularly advantageous about this is that it can be verified whether the storage position allocated to a specific sample container is not already taken up by another sample container.

Another step in the treatment of samples may require sample containers to be verified, at least before they are introduced into the climatic chamber for the first time, which result is then sent to a data processing system.

A camera may be used for such verification which may for example record the state of a sample.

Figure 2:
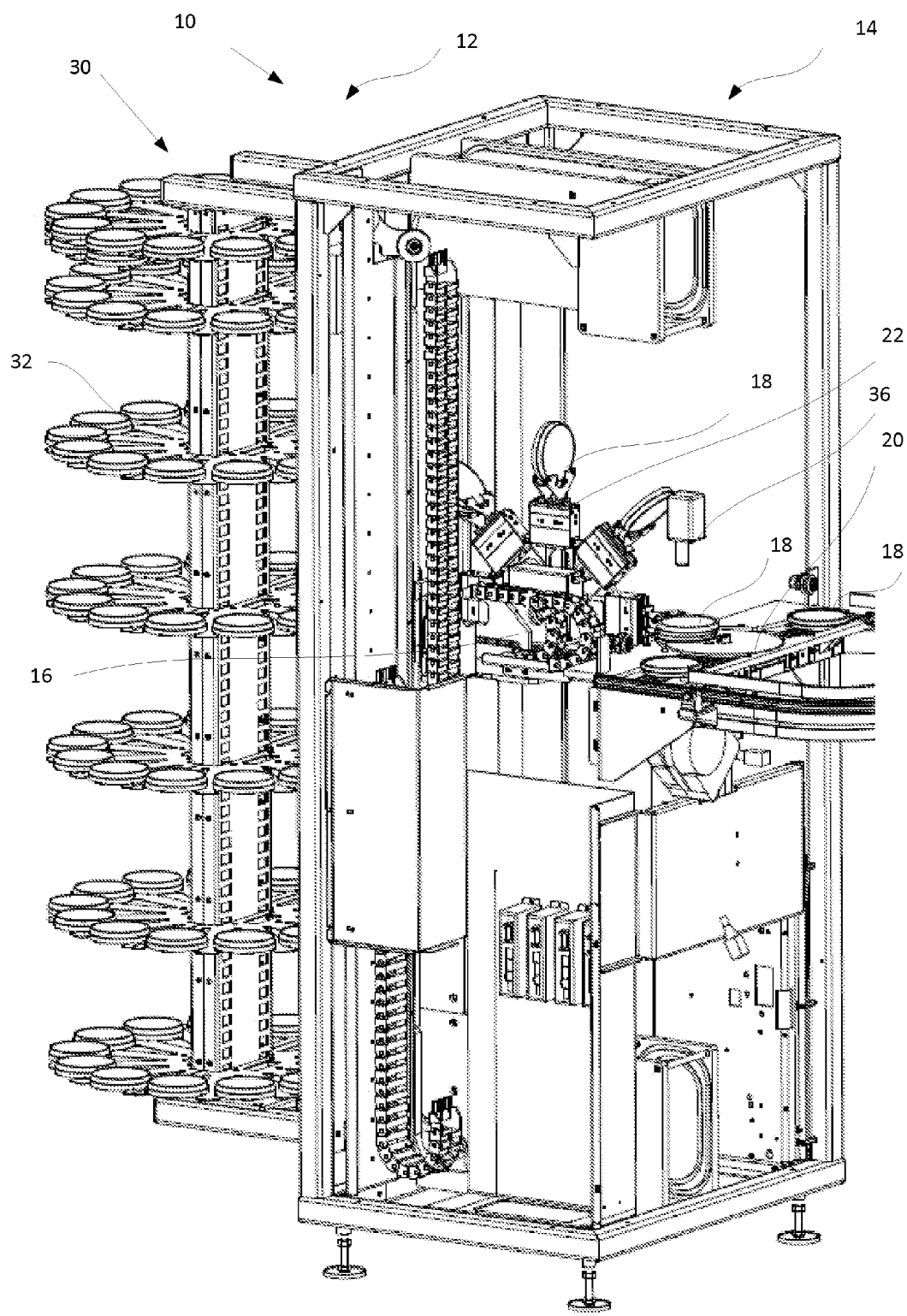
Figure 3:
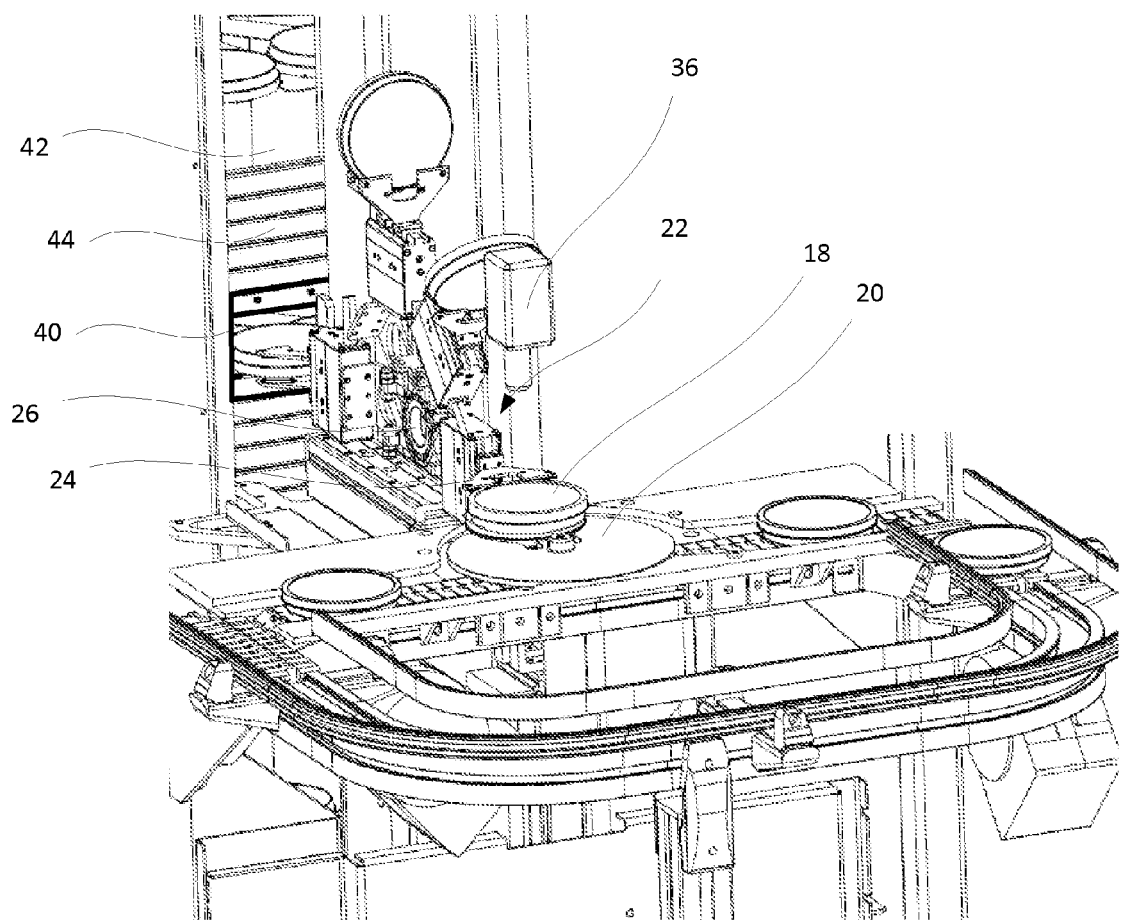

Further advantages, features and possible applications of the present invention may be gathered from the description which follows in which reference is made to the embodiments illustrated in the drawings. Throughout the description, the claims and the drawings, those terms and associated reference numerals are used as are specified in the list of reference numerals which follows below. Of the drawings, FIG. 1 a perspective view of an incubator according to the invention;

FIG. 2 a perspective view of an incubator according to the invention in which the incubator sidewalls are not shown for the sake of clarity;

FIG. 3 a detailed view of the incubator according to the invention.

Shown in FIG. 1 is an incubator 10 according to the invention which comprises a climatic chamber 12 as well as a non-climatic chamber 14 and a connection to a conveying system 16.

Petri dishes 18 are transported by the conveying system 16 to a separating unit 20 which moves them to a receiving position 21 by rotating them. Once they have reached the receiving position 21 they will be picked up and lifted by a gripper arm 22, recorded by a camera 48 and then introduced into and placed within the climatic chamber 12. This operating principle will be described in more detail with reference to FIG. 2.

FIG. 2 is a view of the incubator 10 in which the sidewalls are not shown. The Petri dishes 18 are picked up by the gripper arm 22 and are rotated as they are being introduced into the incubation chamber, i.e. the climatic chamber 12. Provided inside the incubation chamber 12 is a receptacle in which the Petri dishes 18 are placed. This receptacle is in the form of a carousel and comprises a rotatable shaft 32, with individual shelves 34 being removably mounted on said shaft 32. These shelves 34 may be mounted at different heights and spaced differently from each other on said shaft 32, as required.

The Petri dishes 18 are moved through a through passage 40 to a free space opposite said through passage 40. The Petri dishes 18 are transported into the incubation chamber by a feed arm 22 having a gripper 24. The incubator receptacle 30 is movably mounted and motor-driven which thus allows a shelf 34 to be positioned such that a free space on the shelf 34 will be located opposite the through passage 40.

In this way, the gripper 24 provided on the feed arm 22 will only have to travel a short distance to place a Petri dish 18 at a unique position in the climatic chamber 12.

Furthermore, a vertical positioning unit 28 is provided on which the feed arm 22 including the gripper 24 is mounted. This enables the feed arm 22 including the gripper 24 to position and place the Petri dishes 18 at various levels of the incubator receptacle 30. Furthermore, a bar code reader 36 is provided which identifies the labelled Petri dishes 18 and sends such data to a data processing system (not shown). The data processing system allocates a specific position in the incubator receptacle 30 to each Petri dish. Based on this position, the feed arm 22 including the gripper 24 will then be moved vertically, and the incubator receptacle 30 will be positioned such that the allocated storage space will be adjacent to the through passage 40 for the gripper 24. Besides positioning data, time values will also be allocated to the individual sample containers which values may also be stored in the bar code. Such time values may specify for example for how long the individual samples are to be stored in the incubator and whether intermediate analysis will be required for the individual samples.

Once the time value of a certain sample has expired, the feed arm 22 with gripper 24 and the incubator receptacle 30 will again be moved to a respective position in which the Petri dish 18 can be removed from the climatic chamber 12. The sample container 18 will again be rotated and placed on the separating element 20 by means of the feed arm 22 with gripper 24 whereupon the separating element 20 can be moved further in the process line. Before the sample container 18 is placed on the separating element 20, the bar code reader 36 will verify whether the Petri dish 18 removed is actually the right one. This is an additional safeguard against errors.

FIG. 3 shows a detailed view of the feed arm 22 with gripper 24 at a position from which it is clear that the feed arm 22 with gripper 24 is mounted on a bearing 26. Tilting the gripper 24 will allow the Petri dish 18 to be rotated by 180°. Such rotation of the Petri dish 18 has the advantage that any condensation water that may form in the Petri dishes 18 during climatization will not remain on the culture medium of the sample but can drip off onto the lid.

Furthermore, this view shows the through passage 40 through which samples can be introduced into the incubation chamber 12. This passage 40 has been dimensioned such that a Petri dish 18 narrowly fits therethrough. In order to allow samples to pass through at different vertical positions, a vertical opening 42 has been provided in the sidewall 43 in the transition from the climatic chamber to the non-climatic chamber. In this view, however, this opening 42 is covered by a roller-blind type system 44. This roller blind-type system 44 is mounted on the through passage 40 both at its bottom and top ends. Tension pulleys are provided at the bottom and top ends of the vertical opening which will raise or lower the roller blind-type system 44 as the through passage 40 moves up or down. The through passage 40 is connected to the vertical positioning unit 28 on which the feeder 22 with gripper 24 is mounted. The through passage 40 will thus always be properly positioned for the feed arm 22 with gripper 24. Once the gripper 24 is in the proper vertical position, it will merely have to be introduced into the incubation chamber 12 through the through passage 40 by the vertical positioning unit 28 via the feed arm 22 and be inserted into the nearest receptacle of the incubator receptacle 30.

The inventive design of a conditioning chamber allows samples to be handled in an automatic and individualized way which makes it possible to introduce the sample containers into the incubator or remove them from it in a fully automatic way based on individual time specifications. Moreover, such individualized introduction and withdrawal of samples also allows automatic intermediate inspection of the samples.

LIST OF REFERENCE SIGNS 10 conditioning chamber
12 climatic chamber
14 non-climatic chamber
16 conveying system
18 Petri dish, sample container
20 separating unit
21 receiving position
22 feed arm
24 gripper
26 bearing
28 vertically movable positioning unit
30 incubator receptacle
32 shaft
34 shelf
36 bar code reader
40 through passage
42 opening
43 sidewall
44 roller blind-type system
48 camera, detection unit

The invention claimed is:

1. A conditioning chamber (10) for storing samples in a time-controlled manner, comprising:
   a climatically sealed chamber (12);
   a feed device for automatically feeding sample containers (18) into said climatically sealed chamber (12);
   said feed device includes at least one drive, a control unit, and an automatic feed arm (22, 24);
   said climatically sealed chamber (12) having at least one wall (43);
   an opening (40, 42) in said at least one wall (43);
   said sample containers (18) inserted into said climatically sealed chamber (12) through said opening (40, 42);
   an incubator receptacle (30) resides within said climatically sealed chamber (12);
   said incubator receptacle (30) receives said samples (18) within said climatically sealed chamber (12);
   said automatic feed arm (22, 24) resides outside said climatically sealed chamber;
   said feed arm (22, 24) includes a gripper;
   said gripper of said feed arm (22, 24) grips a sample container (18) at a receiving position outside said climatically sealed chamber (12) and moves said sample container (18) to a unique storage position in said incubator receptacle (30);
   said gripper of said feed arm (22, 24) grips a sample container (18) at said storage position within said incubator receptacle (30) and moves said sample container (18) from said climatically sealed chamber (12) to a position outside said climatically sealed chamber, and
   said feed arm (22, 24) rotates during movement of said sample container from said receiving position to said storage position.

2. The conditioning chamber of claim 1, further comprising:
   a positioning unit;
   said positioning unit moves said feed arm (22, 24) vertically; and,
   said feed arm (22, 24) accesses sample container storage positions at different levels within said incubator receptacle (30).

3. The conditioning chamber of claim 1, wherein said opening (42) is in a vertical extension of said sidewall (43).

4. The conditioning chamber of claim 1, wherein said incubator receptacle includes a rotary carousel.

5. The conditioning chamber of claim 4, further comprising:
   a motor;
   said motor resides outside said chamber (12); and,
   said motor drives said rotary carousel (30) via transmission means.

6. The conditioning chamber of claim 1, wherein said climatically sealed chamber (12) is an incubation chamber for cooling and/or heating said containers or an incubator for cooling and/or heating said containers.

7. The conditioning chamber of claim 1, further comprising:
   a conveyor line (16);
   a separation unit (20); and,
   said receiving position is a connection position located at said separation unit (20).

8. The conditioning chamber of claim 1, further comprising:
   a data processing system;
   a bar code reader (36); and,
   said bar code reader evaluates information stored in a bar code on said sample container (18) and forwards said information to said data processing system.

9. The conditioning chamber of claim 1, further comprising:
   a data processing unit;
   a detection unit (48);
   said detection unit assesses the state of a sample within said sample container and stores said assessment in said data processing unit.

10. A conditioning chamber (10) for storing samples in a time-controlled manner, comprising:
    a climatically sealed chamber (12);
    a feed device for automatically feeding sample containers (18) into a climatically sealed chamber (12);
    said feed device includes at least one drive, a control unit and an automatic feed arm (22,24);
    said climatically sealed chamber (12) having at least one wall (43);
    an opening (40, 42) in said at least one wall (43);
    said sample containers (18) inserted into said climatically sealed chamber (12) through said opening (40, 42),
    an incubator receptacle (30) resides within said climatically sealed chamber (12);
    said incubator receptacle (30) receives said samples (18) within said climatically sealed chamber (12);
    said automatic feed arm (22, 24) resides outside said climatically sealed chamber;
    said feed arm (22, 24) includes a gripper;
    said gripper of said feed arm (22, 24) grips a sample container (18) at a receiving position outside said climatically sealed chamber (12) and moves said sample container (18) to a unique storage position in said incubator receptacle (30);
    said gripper of said feed arm (22, 24) grips a sample container (18) at said storage position within said incubator receptacle (30) and moves said sample container (18) from said climatically sealed chamber (12) to a position outside said climatically sealed chamber, and
    said opening is a through passage which can be moved at least vertically.

11. The conditioning chamber of claim 10, further comprising:
    a positioning unit;
    said positioning unit moves said feed arm (22, 24) vertically; and,
    said feed arm (22, 24) accesses sample container storage positions at different levels within said incubator receptacle (30).

12. The conditioning chamber of claim 10, wherein said opening (42) is in a vertical extension of said sidewall (43).

13. The conditioning chamber of claim 10, wherein said incubator receptacle includes a rotary carousel.

14. The conditioning chamber of claim 13, further comprising:
    a motor;
    said motor resides outside said chamber (12); and,
    said motor drives said rotary carousel (30) via transmission means.

15. The conditioning chamber of claim 10, wherein said climatically sealed chamber (12) is an incubation chamber for cooling and/or heating said containers or an incubator for cooling and/or heating said containers.

16. The conditioning chamber of claim 10, further comprising:
- a conveyor line (16);
- a separation unit (20); and,
- said receiving position is a connection position located at said separation unit (20).

17. The conditioning chamber of claim 10, further comprising:
- a data processing system;
- a bar code reader (36); and,
- said bar code reader evaluates information stored in a bar code on said sample container (18) and forwards said information to said data processing system.

18. The conditioning chamber of claim 10, further comprising:
- a data processing unit;
- a detection unit (48);
- said detection unit assesses the state of a sample within said sample container and stores said assessment in said data processing unit.

\* \* \* \* \*